US00PP31121P2

(12) United States Plant Patent
Rouwette

(10) Patent No.: US PP31,121 P2
(45) Date of Patent: Nov. 26, 2019

(54) ***HYDRANGEA* PLANT NAMED 'GRHYAR1406'**

(50) Latin Name: *Hydrangea arborescens*
Varietal Denomination: GRHYAR1406

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 16/350,319

(22) Filed: Nov. 1, 2018

(30) Foreign Application Priority Data

Aug. 10, 2018 (EM) ..... 20182083

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea arborescens* plant named 'GRHYAR1406' that is characterized by its sturdy stems, its compact plant habit, and its large inflorescences that are light pink in color.

2 Drawing Sheets

Botanical classification: *Hydrangea arborescens*.
Varietal denomination: 'GRHYAR1406'.

CROSS REFERENCE TO A RELATED APPLICATION

This application is co-pending with a U.S. Plant Patent Application filed for a plant derived from the same breeding program that is entitled *Hydrangea* Plant Named 'GRHYAR1407' (U.S. application Ser. No. 16/350,320).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Hydrangea arborescens* and will be referred to hereafter by its cultivar name, 'GRHYAR1406'. 'GRHYAR1406' represents a new smooth *hydrangea*, a perennial shrub grown for landscape use.

'GRHYAR1406' derived from an ongoing breeding program by the Inventor in Valkenburg, The Netherlands. 'GRHYAR1406' arose as a controlled cross between an unnamed proprietary plant of *Hydrangea arborescens* from the Inventor's breeding program and *Hydrangea arborescens* 'Annabelle' (not patented) as the male parent in 2011. 'GRHYAR1406' was selected a single unique plant from amongst the resulting seedlings in summer of 2014.

Asexual propagation of the new cultivar was first accomplished by stem cuttings by the Inventor in summer of 2014 in Valkenburg, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRHYAR1406' as a unique cultivar of *Hydrangea arborescens*.

1. 'GRHYAR1406' exhibits sturdy stems.
2. 'GRHYAR1406' exhibits a compact plant habit.
3. 'GRHYAR1406' exhibits large inflorescences that are light pink in color.

The female parent of 'GRHYAR1406' differs from 'GRHYAR1406' in having a less compact plant habit. The male parent of 'GRHYAR1406', 'Annabelle', differs from 'GRHYAR1406' in having white flowers and weaker stems. 'GRHYAR1406' can also be most compared to *Hydrangea arborescens* cultivars 'Abetwo' (U.S. Plant Pat. No. 20,571), 'NCHA1' (U.S. Plant Pat. No. 20,765) and 'GRHYAR1407', 'Abetwo' is similar to 'GRHYAR1406' in having strong stems. 'Abetwo' differs from 'GRHYAR1406' in having inflorescences that are white in color and in having a larger plant size. 'NCHA1' is similar to 'GRHYAR1406' in having pink inflorescences. 'NCHA1' differs from 'GRHYAR1406' in having a larger plant size. 'GRHYAR1407' is similar to 'GRHYAR1406' in having pink inflorescences. 'GRHYAR1407' differs from 'GRHYAR1406' in having darker pink inflorescences, a larger plant size and foliage that is bronze-green in color.

BRIEF DESCRIPTION OF THE DRAWINGS

The accompanying colored photographs illustrate the overall appearance and distinct characteristics of the new

*Hydrangea*. The photographs were taken of a plant three years in age as grown outdoors in a 10-liter container in Boskoop, The Netherlands.

Figure 1:
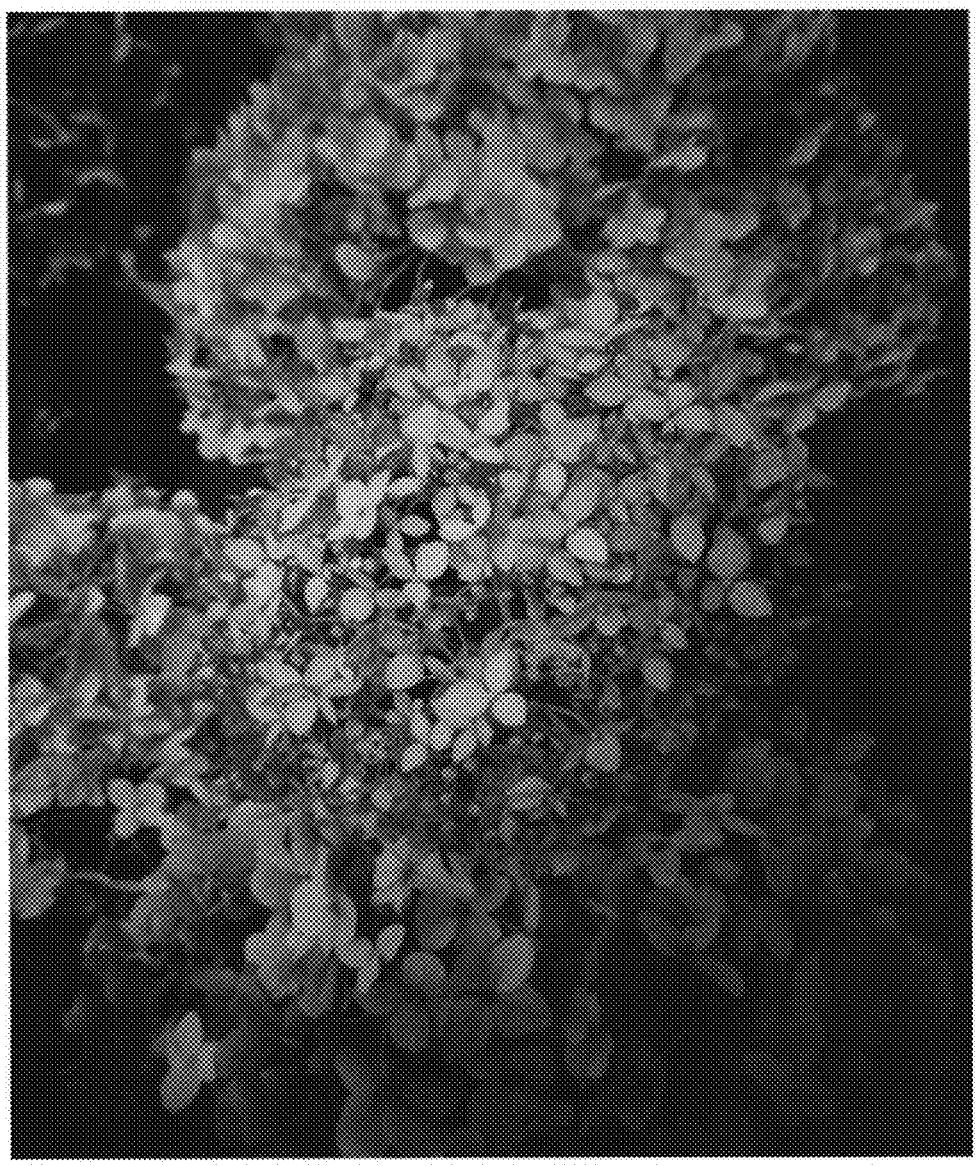

The photograph in FIG. 1 provides a view of a newly open inflorescence of 'GRHYAR1406' with aging inflorescences shown in the background.

Figure 2:
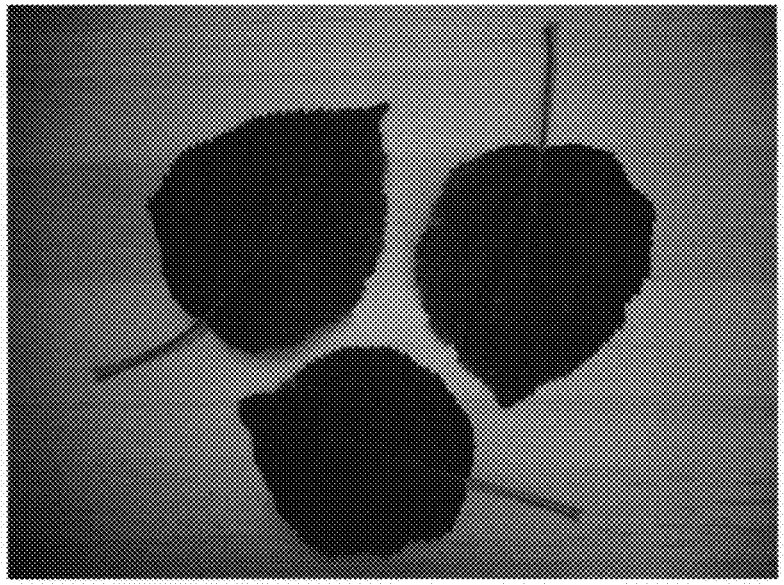

The photograph in FIG. 2 provides a close-up view of the leaves of 'GRHYAR1406'.

Figure 3:
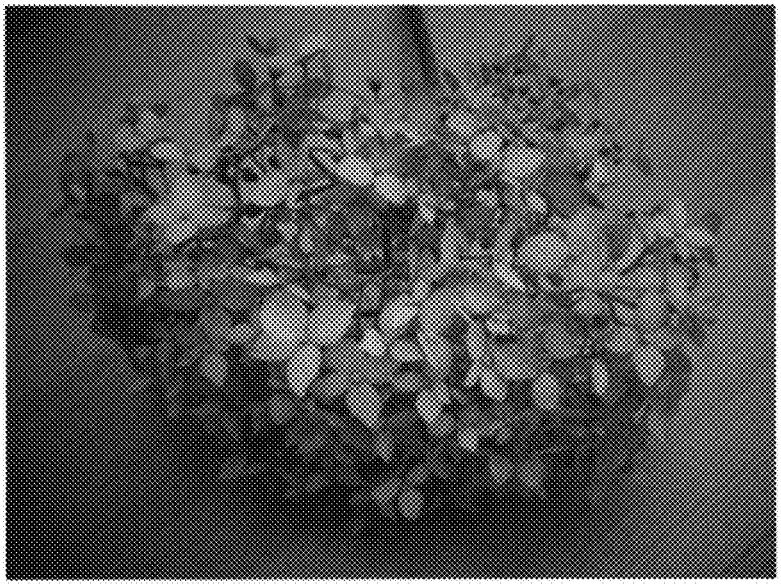

The photograph in FIG. 3 provides a close-up view of a newly opened inflorescence of 'GRHYAR1406'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants three years in age as grown outdoors in 10-liter containers in Boskoop, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period*.—From July to September in The Netherlands.

*Plant type*.—Perennial shrub with mophead-like corymbs.

*Plant habit*.—Compact with sturdy stems, broadly ovate in shape.

*Height and spread*.—Reaches 80 to 100 cm in height and 80 cm in spread as a 3-year-old plant in the landscape.

*Cold hardiness*.—At least to U.S.D.A. Zones 5b.

*Diseases and pests*.—No susceptibility and resistance to pests and diseases has been observed.

*Root description*.—Fibrous and 155B in color.

*Propagation*.—Stem cuttings.

*Time required for root development*.—6 to 8 weeks for root initiation with a plant finished in a P9 container in about 12 months from a rooted cutting.

*Growth rate*.—Moderate to vigorous.

Stem description:

*Stem shape*.—Round.

*Stem color*.—New growth; 183B, mature wood and bark; N167B.

*Stem size*.—60 to 100 cm in length and 5 to 7 mm in diameter.

*Stem surface*.—Glabrous, no lenticels present.

*Stem aspect*.—Average angle 60° to 90° (soil level=0°).

*Internode length*.—6 to 12 cm.

*Branching*.—Average of 10 to 20 branches from base after 1 hard prune.

*Stem strength*.—Strong.

Foliage description:

*Leaf shape*.—Broadly ovate to elliptic.

*Leaf division*.—Simple.

*Leaf size*.—An average of 13 cm in length and 9 cm in width.

*Leaf base*.—Obtuse to subcordate.

*Leaf apex*.—Acute to subacuminate.

*Leaf venation*.—Pinnate, color upper and lower surface on mature leaves; 146D.

*Leaf margins*.—Coarsely serrate.

*Leaf attachment*.—Petiolate.

*Leaf arrangement*.—Opposite.

*Leaf surface*.—Upper and lower surface smooth and glabrous with mid vein sparsely short hairy.

*Leaf color*.—Immature leaves upper surface; 144A, immature leaves lower surface; 144B, mature leaves upper surface; 146A, mature leaves lower surface; 146B.

*Petioles*.—Up to 6 cm in length and 2 to 3 mm in diameter, upper surface; sparsely short hairy, 144C in color with slight tint of 176A, lower surface; glabrous and 144C in color.

Inflorescence description:

*Inflorescence type*.—Terminal mop-head; cymose corymb, comprised of showy flowers and fertile flowers.

*Lastingness of inflorescence*.—Up to 8 weeks.

*Inflorescence number*.—One per stem.

*Inflorescence size*.—Average of 17 cm in height and 23 cm in diameter.

*Inflorescence bracts*.—An average of 3, an average of 2 cm in length and 4 mm in width, ovate to elliptic in shape, apex long acuminate, base cuneate, margin entire, surface slightly arachnoid, 144A in color, occasionally present on fertile flower; filiform in shape and 1.5 mm in length, other characteristics similar to inflorescence bracts.

*Flower fragrance*.—No fragrance.

*Flower buds*.—Showy flowers; average of 1.5 mm in length and 1 mm in diameter, ovate in shape, 144D in color and 64D at apex, glabrous surface, fertile flowers; an average of 1 mm in length and 1.5 mm in diameter, broadly ovate in shape, 145D in color with flush of 59A, glabrous surface.

*Showy flowers*.—800 to 1,000 per inflorescence, rotate. held outward, 3 mm in depth, 1 to 2.5 cm in diameter, last 6 to 8 weeks, persistent.

*Fertile flowers*.—An average of 500 to 700 per inflorescence, rotate, held upright, 3 mm in depth, 5 mm in diameter, last about 3 days, self-cleaning.

*Peduncles*.—Strong, 2 to 4 cm in length and 1 to 4 mm in width, 144B in color and slightly flushed with 59A, surface short hairy.

*Pedicels*.—Showy flowers; 8 mm to 2.8 cm in length, 5 mm in width, held at an angle between 30° to 90°, strong, 150D in color, surface short hairy, fertile flowers; 2 to 3 mm in length, 0.5 mm in width, typically held at a 90° angle, moderately strong, 150D in color, surface short hairy.

*Petals*.—Showy flowers; 2 to 3, rotate in arrangement, cymbiform in shape, entire margin, acute apex, cuneate base, up to 1 mm in length and 0.5 mm in width, upper and lower surface glabrous, color; upper and lower surface when opening and mature 69C with background of 145D, quickly fleeting, fertile flowers; 5, rotate in arrangement, triangular in shape, an average of 3 mm in length and width, acute apex, truncate base, entire margins, upper and lower surface glabrous, color; when opening upper and lower surface 150D, upper and lower surface when fully open; 145D.

*Sepals*.—Showy flowers; 3 to 4, rotate in arrangement, broadly ovate to broadly elliptic in shape, entire margin, acute apex, cuneate base, up to 1.2 cm in length and 1.1 cm in width, upper and lower surface glabrous with a few hairs at base, color; upper surface when opening 150D with very thin veins and apex 68D, lower surface when opening 68D and 150D at base, fully open upper and lower surface; a blend of 68D and NN155C, upper and lower surface fading; 149D with veins 144D, fertile flowers; 5, rotate in arrangement, small elliptic in shape, acute apex, broad cuneate base, entire margin, an average of 1.5 mm in length and 8 mm in width, both surfaces glabrous and matte, color; upper and lower surface when opening and fully open 158D, quickly fleeting.

Reproductive organs:

*Presence*.—Both showy and fertile flowers are perfect.

*Stamens*.—Showy flowers; 6 to 7, filament is 1 to 3 mm in length, 155D in color with glabrous surface, anther is orbicular in shape, 0.3 mm in length and 155D in color, pollen is very low in quantity if present and 155D in color, fertile flowers; 9 or 10, filament is 1 to 4 mm in length and 155D in color, anther is orbicular in shape, 0.3 mm in length and 155D in color, pollen is low in quantity and 155D in color.

*Pistils*.—Showy flowers; 1, an average of 1 mm in length, stigma is club-shaped or reduced, stigma, style, and ovary 155D in color, fertile flowers; 2, an average of 1 mm in length, stigma is obovate in shape, stigma, style, and ovary 155D in color.

*Fruit and seed*.—No fruit or seed production has been observed to date.

It is claimed:

1. A new and distinct cultivar of *Hydrangea* plant named 'GRHYAR1406' substantially as herein illustrated and described.

* * * * *